United States Patent [19]

Khait

[11] 4,300,885
[45] Nov. 17, 1981

[54] PERCUSSIVE DENTAL CROWN EXTRACTOR

[76] Inventor: George Khait, 516 28th Ave., #3, San Francisco, Calif. 94121

[21] Appl. No.: 172,860

[22] Filed: Jul. 30, 1980

[51] Int. Cl.³ ............................................... A61C 3/08
[52] U.S. Cl. ..................................... 433/151; 433/121
[58] Field of Search ................................ 433/121, 151

[56] References Cited

U.S. PATENT DOCUMENTS

| | | | |
|---|---|---|---|
| 74,629 | 2/1868 | Taylor | 433/121 |
| 858,914 | 7/1907 | Shannon | 433/121 |
| 927,420 | 7/1909 | Lyle | 433/121 |
| 1,001,638 | 8/1911 | Guhitz | 433/121 |
| 2,337,971 | 12/1943 | Caviglia | 433/121 |
| 2,776,490 | 1/1957 | Carfagni | 433/121 |
| 3,254,412 | 6/1966 | Armao | 433/121 |
| 3,686,756 | 8/1972 | Pankratz | 433/121 |

OTHER PUBLICATIONS

JADA, vol. 99, 1979, pp. 840 to 849 by R. A. Oliva, "Review of Methods for Removing Cast Gold Restorations".

Primary Examiner—Robert Peshock
Attorney, Agent, or Firm—David Pressman

[57] ABSTRACT

A percussive dental crown extractor comprises a hook 16 attached by an arm 14 to the front end of a tube 12 which encloses a cylindrical, notched hammer 44 and a spring 50 urging the hammer to the rear end of the tube, remote from the hook. The tube is telescoped into an outer cylinder 10. The tube and cylinder are held together by an axial post 38, one end of which is attached to the bottom 32 of the cylinder, the other end of which extends through an opening in the rear 36 of the tube and has a captivating cap 40 inside the tube. A spring 42 around the post urges the tube and cylinder apart. A sear 52 mounted in a boss 20 in the side of the tube, engages a notch 46 on the hammer when the hammer is moved to the front end 34 of the tube by compressing the cylinder and tube. When the cylinder and tube are relaxed, the hammer and its spring are held cocked by the sear. When the sear is pulled out of the hammer by a finger release 22, the hammer flies back to hit the post cap, which in turn hits the rear end of the tube, causing the tube, and hence the hook, to jolt rearwardly.

10 Claims, 4 Drawing Figures

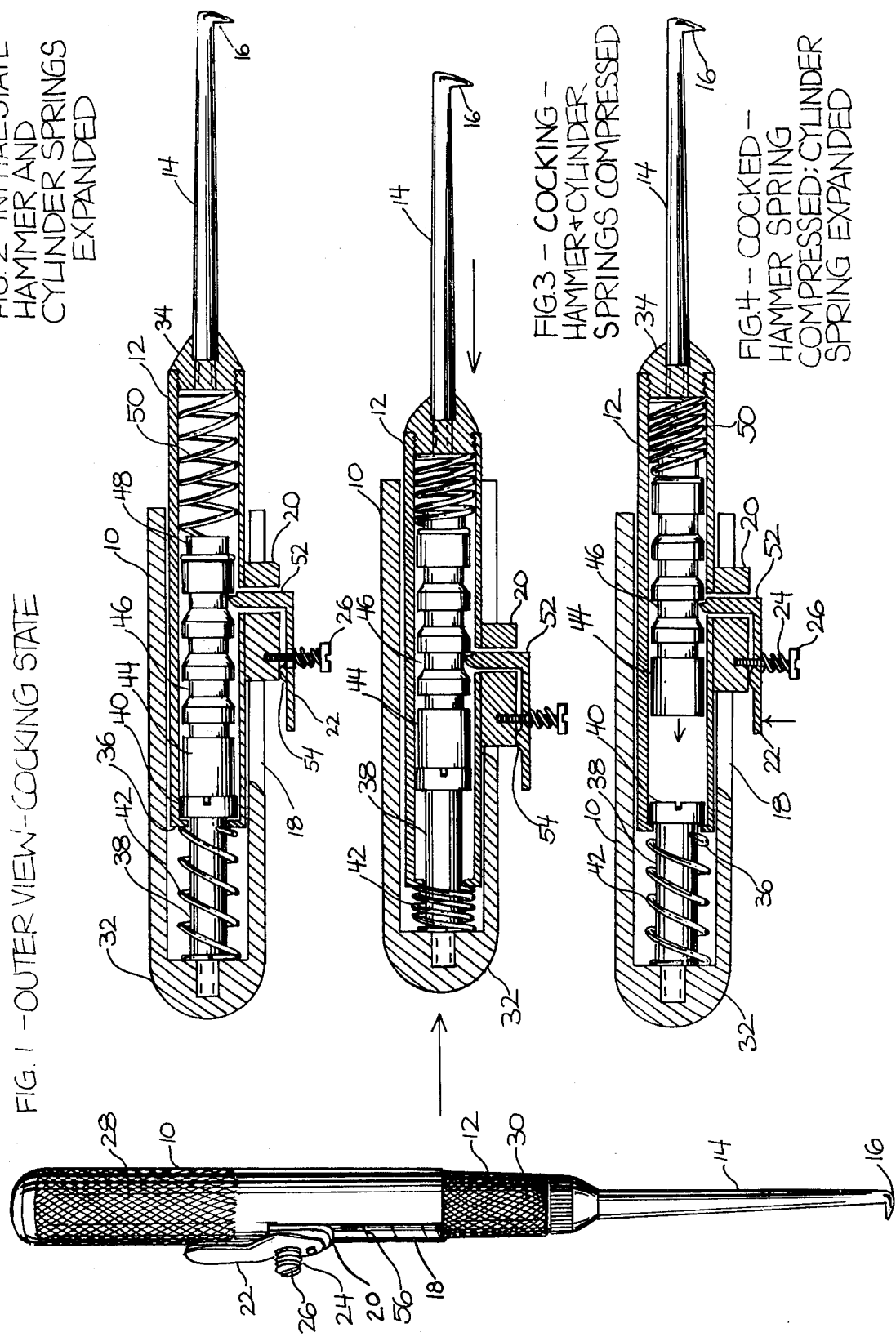

4,300,885

PERCUSSIVE DENTAL CROWN EXTRACTOR

BACKGROUND

1. Field of Invention

This invention relates to a dental crown extractor, particularly to such an extractor employing self-contained percussive means.

2. Description of Prior Art

In dentistry, it is sometimes necessary to remove a cast restoration (crown) of gold or other material which is attached to or arround the occlusal surface of a tooth by cementation. Prior art removal methods comprised grinding off the crown; drilling a hole and prying off the crown; use of a mallet and chisel; use of a screw and wrench or other types of screw-lever devices; use of a slaphammer; use of hydraulic elevators; use of various prying instruments; and use of adhesive removers operable by the patient's own jaws. Each of these methods had significant drawbacks; they were either awkward to implement, created excessive force, thereby tending to damage the restored tooth, required excessive labor, required expensive and unreliable instrumentation, damaged the crown itself unnecessarily, and/or had various other drawbacks.

Accordingly several objects of the present invention are to overcome the aforementioned drawbacks of prior art crown removers. Further objects and advantages will become apparent from a consideration of the ensuing description.

DRAWINGS

FIG. 1. is an isometric view of the crown remover of the invention, shown during maximum cocking.

FIGS. 2, 3 and 4 are partial sectional views of the crown remover in its following respective states: initial, during cocking, and cocked.

REFERENCE NUMERALS

| | | |
|---|---|---|
| 10 cylinder | 12 tube | 14 extension arm |
| 16 hook on 14 | 18 slot in 10 | 20 boss in 14 |
| 22 finger release | 24 spring | 26 post |
| 28 knurls on 10 | 30 knurls on 12 | 32 rear end of 10 |
| 34 cap of 12 | 36 rear end of 12 | 38 sear post |
| 40 cap on 38 | 44 hammer | 42 cylinder spring |
| 46 notches on 44 | 48 stub on 44 | 50 hammer spring |
| 52 sear arm | 54 pivot boss on 22 | 56 lines on 12 |

DESCRIPTION OF INVENTION

The crown remover of the invention (FIG. 1) comprises an outer cylinder 10 into which is telescoped a tube 12 having extension arm 14 with a hook or grasping means 16 at the distal end thereof. Cylinder 10 has a partial slot 18 extending from the forward end thereof (nearest hook 16) and tube 12 has on the side thereof a boss 20 which is keyed into slot 18. Boss 20 and slot 18 cooperate to allow tube 12 to move axially without rotation in cylinder 10. On boss 20 is mounted a finger release or sear operator 22, the forward end of which is held against 20 by a helical spring 24 which is mounted around a post 26. The rear end of release 22 is spaced from cylinder 10 as indicated. The rear end of cylinder 10 is knurled at 28, as is the front end of tube 10 at 30.

All of the external parts of the device preferably are made of stainless surgical steel, except extension arm 14 and hook 16, which are made of spring steel of the type used for dental explorers. A shroud (not shown) may be provided to cover slot 18 and the forward end of release 22 and post 26.

As shown in FIG. 2, cylinder 10 is open at its forward end to receive tube 12 and is closed at its rear end 32. The forward end of tube 12 is closed by a cap 34 which is screwed into cylinder 12, with extension arm 14 in turn being screwed into cap 34. The rear end 36 of tube 12 has an opening therein.

A post 38 is mounted axially in cylinder 10 by being screwed into rear end 32 thereof. The forward end of post 38 extends through the opening in rear end 36 of tube 12 and has a cap 40 thereon, thereby to captivate tube 12 in cylinder 10. A helical first or cylinder spring 42 is mounted around post 38, between rear end 32 of cylinder 10 and rear end 36 of tube 12.

Within tube 12 is positioned a generally cylindrical hammer 44 having four notches such as 46 thereon. The rear end of hammer 44 is smooth and the forward end has a stub 48 of reduced diameter. A helical second or hammer spring 50 is mounted around stub 48 and between hammer 44 and front end 34 of tube 12. The outer diameter of hammer 44 is almost equal to the inner diameter of tube 12 so that hammer 44 can move axially within tube 12 without appreciable side play.

Finger release 22 is connected to a sear arm 52 so that the assembly 22–52 is L-shaped. Sear arm 52 extends into tube 12 via a hole in boss 20 and has a tip or catch portion in engagement with one of notches 46 on hammer 44. The rear side of the tip of sear 52 is faired and the forward side is straight and notched. Finger release 22 is held to boss 20 by post 26 which is screwed into boss 20 through a hole in finger release 22. Finger release 22 has an integral pivot boss 54 mounted thereon to enable it to be pivoted or rocked on boss 20.

All of the parts shown have circular cross sections, except springs 42 and 50, hook 16, slot 18 of cylinder 10, and boss 20 and its associated sear components 22, 24, 26, 52, and 54.

The device is shown to approximate scale. Its approximate major dimensions are as follows: overall length of cylinder 10, 95 mm; overall length of tube 12 with arm 14 and hook 16, 180 mm; outer diameter of cylinder 10, 14 mm; outer diameter of tube 12, 12 mm; length of hammer 44, 40 mm; length of post 38 (excluding threaded rear tip), 40 mm; outer diameter of hammer 44, 10 mm; depth of notches on hammer 44, 3 mm; and wire diameter and relaxed length of springs 42 and 50, 1 mm, and 55 mm, respectively.

OPERATION

The extractor is operated by pushing tube 12 further into cylinder 10 to cock hammer 44. Then tube 12 is released, allowing it to return to its original position. Hook 16 is engaged onto the margin of the crown to be extracted, and finger release 22 is pressed, allowing hammer 44 to fly back to its initial position, thereby giving a rearward jolt to hook 16, which will loosen the crown.

More specifically, as shown in FIG. 2 (initial state), a large portion of tube 12 is outside cylinder 10, cylinder spring 42 is almost completely relaxed, and hammer spring 50 also is almost completely relaxed and urges hammer 44 rearwardly in tube 12, against cap 40 of post 38.

To cock the device, tube 12 is pushed further into cylinder 10 as indicated by the arrows in FIG. 3. This will compress cylinder spring 42 as indicated. Post 38, being attached to cylinder 10, will cause hammer 44 to move forwardly with respect to tube 12, thereby also compressing hammer spring 50 as indicated. During the cocking motion, a series of clicks will be heard as the faired side of the tip of sear 52 passes and the whole tip of sear 52 rides in and out of successive notches 46 of hammer 44. FIG. 3 shows sear 52 engaged in the third notch from the forward end of hammer 44. If greater percussive operating force is desired, tube 12 can be pushed further into cylinder 10 (as shown in FIG. 1), so that the fourth notch of hammer 44 will be engaged by sear 52. On the other hand, if less percussive force is desired, tube 12 can be pushed a shorter distance into cylinder 10, i.e., until only the first click is heard, whereby sear 52 will engage the second notch in hammer 44. Tube 12 has a series of lines 56 thereon (FIG. 1) corresponding to notches 46 on hammer 44; the degree of compression or energy stored can be determined by the count of the number of lines in slot 18.

Next (FIG. 4) tube 12 is released, allowing it to be urged out of cylinder 10 by relaxation of cylinder spring 42. Since hammer 44 is held at the forward end of tube 12 by the straight, notched side of the tip of sear 52, post 38 and hammer 44 will separate, as indicated. Hammer spring 50 thus will remain compressed, as also indicated.

Next, while the extractor is hand-held, hook 16 is engaged firmly under a suitable lingual or buccal margin of the crown to be extracted. Finger release 22 is pressed as indicated by the arrow. This will cause sear 52 to be pulled out of engagement with notch 46 of hammer 44 and spring 50 will thereupon cause hammer 44 to fly rapidly rearwardly (vide arrow) until it strikes and is snubbed by cap 40 of post 38. The resulting percussive reaction will be transmitted to tube 12, causing hook 16 to make an incremental rearward motion, which will tend to loosen and extract the crown from its tooth.

The process can be repeated as many times as necessary with great facility since the extractor can be cocked by simple push-pull motions applied to cylinder 10 and tube 12.

Since, according to the invention, only a jolt or minor incremental motion of hook 16 occurs, the extractor of the invention will be very unlikely to hurt or otherwise loosen the underlying tooth.

ASSEMBLY

The device can be disassembled and assembled readily for cleaning and sterilization. To assemble a disassembled device, cylinder spring 42 is placed in cylinder 10, followed by tube 12. (Boss 20 on tube 12 is keyed into slot 18 of cylinder 10 during insertion of tube 12 into cylinder 10.) Then post 38 is placed in tube 12 through the hole in sear end 36 of tube 12. The threaded tip of post 38 then is screwed into end wall 32 of cylinder 10; cap 40 of post 38 has a screw slot for this operation. Then hammer 44 and hammer spring 50 are placed in tube 12. Cap 34 and extension arm 14 are threaded respectively into tube 12. Lastly sear assembly 22–52 is positioned within the hole of boss 20, and spring 24 and screw 26 are assembled to boss 20, as indicated.

SCOPE OF INVENTION

While the invention has been described by way of specific example, this should be considered exemplary and not limiting. Various other modifications and ramifications of the invention will occur to those skilled in the art. For example, in lieu of a dental crown extractor, the device may be used as a slaphammer, tapper, or mallet, whereby it will provide incremental blows for delicate assembly or removal operations. Therefore the full scope of the invention should be determined only by the appended claims and their legal equivalents.

I claim:

1. A percussive device comprising, in combination:
   a cylinder,
   a tube telescoped into said cylinder for axial movement with respect thereto,
   a hammer slidably mounted for axial movement within said tube,
   means urging said hammer in an axial direction to a first position in said tube,
   coupling means for moving said hammer to a cocked position axially away from said position in response to movement of said tube in an axial direction with respect to said cylinder, and
   sear means for releasably holding said hammer in said cocked position, whereby actuation of said sear means when said hammer is in said cocked position will allow said hammer to fly back to said first position in said tube and thereby cause a percussive reaction within and consequent limited movement of said device.

2. The device of claim 1 further including external grasping means attached to one end of said tube, whereby said device may be used as a dental crown extractor.

3. The device of claim 1 wherein said hammer has notches thereon and said sear means comprises a catch extending through said tube and a slot in said cylinder to a finger release on the outside of said cylinder, said catch shaped to engage any of said notches on said hammer.

4. The device of claim 1 wherein said coupling means comprises a post positioned in and attached to one end of said cylinder, one end of said post extending into said tube.

5. The device of claim 4 wherein said tube has an end wall with an opening therein through which said one end of said post extends, and further including a helical spring mounted around said post to urge said tube and cylinder apart, one end of said post having a cap thereon which is larger than said opening in said end wall of said tube so that said post limits the axial position of said tube in said cylinder.

6. The device of claim 1 wherein said hammer is elongated and generally cylindrical in shape and has an outer diameter almost equal to the inner diameter of said tube.

7. The device of claim 1 wherein said tube has two end walls at the respective ends thereof, one end wall of said tube being outside cylinder and having an extension arm with a hook at the end of said arm attached thereto, the other end wall of said tube being inside said cylinder, said cylinder having one end wall thereon, a spring in said cylinder between said end wall of said cylinder and said other end wall of said tube for urging said tube and cylinder apart.

8. The device of claim 7 wherein said cylinder has a post therein, one end of said post attached to said end wall of said cylinder, the other end of said post extending through an opening in said other end wall of said tube, said other end wall of said post having a cap thereon which is larger than said opening so as to limit the axial position of said tube in said cylinder.

9. The device of claim 1 wherein said tube has a slot therein, said tube has a boss on the side wall thereof, said boss extending through said slot and having a hole therein, said sear means being mounted in said boss.

10. The device of claim 9 wherein said hammer has notches thereon, said sear means comprises an L-shaped catch member, one leg of which extends through said boss for engaging said notches, the other end of which is lockably mounted on said boss, and including means for urging said one end of said catch member into said notches of said hammer.

* * * * *